United States Patent [19]

Suh et al.

[11] Patent Number: 5,962,287
[45] Date of Patent: Oct. 5, 1999

[54] PROCESS FOR PRODUCING ERYTHRITOL USING MUTANT TRICHOSPORONOIDES

[75] Inventors: Seung Hyun Suh, Seoul; Dae Chul Kim; Young Je Cho, both of Kyungkeedo; Yeang Joong Jeon; Jae Heung Lee, both of Seoul, all of Rep. of Korea

[73] Assignee: Cheil Jedang Corporation, Seoul, Rep. of Korea

[21] Appl. No.: 08/863,573

[22] Filed: May 27, 1997

[30] Foreign Application Priority Data

Mar. 26, 1997 [KR] Rep. of Korea ............ 97-11342

[51] Int. Cl.$^6$ .................................................. C12P 7/18
[52] U.S. Cl. ........................................ 435/158; 435/254.11
[58] Field of Search .................... 435/158, 254.11

[56] References Cited

PUBLICATIONS

Derwent Abstract 97–367068/34 JP09154589 Mitsubishi Chem Corp Jun. 17, 1997.

*Primary Examiner*—Herbert J. Lilling
*Attorney, Agent, or Firm*—Burns, Doane, Swecker & Mathis, L.L.P.

[57] ABSTRACT

A novel *Trichosporonoides madida* CJ-NT1 microorganism which is capable of converting fermentable sugars to a high titre of erythritol under low aeration conditions and a method of producing erythritol by fermentation of sugar, which comprises culturing the cells of the *Trichosporonoides madida* CJ-NT1 strain are provided.

14 Claims, No Drawings

PROCESS FOR PRODUCING ERYTHRITOL USING MUTANT TRICHOSPORONOIDES

FIELD OF THE INVENTION

The present invention relates to a novel microorganism and a method for preparing erythritol by fermentation using the same. More specifically, the present invention relates to an artificial mutant *Trichosporonoides madida* CJ-NT1 strain and a method for preparing erythritol by converting fermentable sugar to erythritol with the said strain.

BACKGROUND OF THE INVENTION

It is well-known to prepare erythritol by fermentation using microorganisms. The microorganisms so far known to be capable of producing erythritol include, for instance, those belonging to Aureobasidiun sp. (Japanese Patent Laid-Open Publication No. 61-31091), Moniliella sp. (EP Publication No. 0,136,805), *Candida zeylanoides* (Japanese Patent Laid-Open Publication No. 49-118889), *Candida lipolytica* (U.S. Pat. No. 3,756,917), Debaryomyces sp. (U.S. Pat. No. 2,986,495), Pichia sp. (U.S. Pat. No. 2,986,495), Moniliella sp. (Antonie van Leeuwenhoek, 37, 107–118 (1971) and Applied Microbiology, 12(3), 240—246 (1964)), and the like.

However, such known microorganisms have not still been used on an industrial scale due to their grave disadvantages that cannot practically be neglected.

More exactly, Japanese Patent Laid-Open Publication No. 61-31091 and EP Publication No. 0,136,805 describe methods for preparing erythritol from monosaccharides with the use of Aureobasidium sp. and Moniliella sp. microorganisms, respectively. These methods make it possible to prepare erythritol using a relatively high substrate concentration of a culture media and, hence, are valuable in their own ways. However, these methods are not always satisfactory owing to the disadvantages that a large amount of antifoamer should be added since marked foaming occurs at the time of culture. Furthermore, Japanese Patent Laid-Open Publication No. 61-31091 is disadvantageous in that the yield of erythritol are not only unsatisfactory relative to the amount of cells grown by microorganisms, but the optimum pH, temperature and the like are also narrow, and, even if such factors depart slightly from the optimum ranges, there is then a remarkable drop of the yield of erythritol.

U.S. Pat. No. 2,986,495 discloses a method for preparing arabitol, glycerol and erythritol from monosaccharides with the use of Pichia sp. and Debaryomyces sp. microorganisms. According to this method, however, while glycerol and arabitol would be produced as the major product, only a small amount of erythritol may be produced as the byproduct, which should be separated out and collected with considerable difficulty.

U.S. Pat. No. 3,756,917 teaches a method for the preparation of erythritol from hydrocarbons using Candida sp. microorganisms. However, this method is of low productivity and so uneconomical due to the need that the substrate concentration be at most 20%. Another potential disadvantage is the possibility that the starting hydrocarbons may remain in the product.

Antonie van Leeuwenhoek, 37, 107–118 (1971) and Applied Microbiology, 12(3), 240–246 (1964) describes a method for preparing erythritol from glucose with the use of Moniliella (Torula) sp. microorganisms. This method is characterized in that the ratio of conversion of glucose to erythritol is high and the substrate concentration of a culture media may be increased to a relative high level, but has the disadvantage that a large amount of xanthane gum should be used for defoaming, since marked foaming occurs at the time of culture.

It has been found by the present inventors that erythritol can be produced by *Trichosporonoides madida* isolated from a honeycomb. However, the ability of this wild T madida to produce erythritol was not high enough for industrial use.

A novel high erythritol producing strain *T. madida* KCTC 8712P having high osmotic tolerance was developed by the present inventors. This strain was prepared by treating the above wild-type erythritol producing *T. madida* with a mutagenic agent N-methyl-N'-nitro-N-nitrosoguanidine. However, a method of producing erythritol using *T. miadida* KCTC 8712P strain are not practical since lots of foaming occur during culture and thus reduce the efficiency of the fermentor.

In view of the fact that reducing aeration rate makes it possible to decrease the foams occurred during culture, the present inventors strived to develop *T. madida* strains requiring a less oxygen supply while maintaining the high erythritol productivity.

SUMMARY OF THE INVENTION

Therefore, an object of the present invention is to provide a novel microorganism which shows high erythritol productivity and is of high industrial significance.

Another object of the present invention is to provide a novel microorganism which can keep high erythritol productivity even in a limited oxygen supply condition to reduce the occurrence of foaming during fermentation.

A further object of the present invention is to provide a method of obtaining such a microorganism.

A still further object of the present invention is to provide a method for efficiently producing erythritol with the use of such a microorganism as mentioned above.

DETAILED DESCRIPTION OF THE INVENTION

The present invention provides a novel *T. madida* CJ-NT1 microorganism which is capable of converting fermentable sugars to a high titre of erythritol under a low aeration condition, i.e., less than 0.5 v/v/m (aeration volume/medium volume/minute), preferably less than 0.3 v/v/m.

The inventive *T. madida* CJ-NT1 strain was deposited at the permanent collection of the Korean Culture Center of Microorganisms, Seoul, Korea, on Mar. 18, 1997 under the Budapest Treaty on the international recognition of the deposit of microorganisms for the purposes of patent procedure, and a subculture of the microorganism can be obtained from the repository under the accession number KCCM-10098.

The inventive *T. madida* CJ-NT1 strain was prepared by treating osmophilic *T madida* KCTC 8712P with a mutagenic agent. The method for obtaining such a mutant will now be explained.

The *T madida* KCTC 8712P strain whose subculture can be obtained from the Korean Culture Center of Microorganisms under the accession number KCCM-10098, was aerobically cultured on a liquid culture medium having 22% (w/v) of glucose or sucrose and 1% (w/v) of yeast extract for three (3) days. After centrifugation, an aqueous supernatant was discarded, and a sedimented microbes was diluted with the same sterile liquid medium which was in turn treated with 1 mg/ml of N-methyl-N'-nitro-N-nitrosoguanidine in a buffer solution. Subsequently, the thus treated cells were cultured on a liquid culture medium having Yeast Nitrogen Base (Difco) supplemented with 1% (w/v) of glucose and 20 mg/l of sodium azide for three (3) days. The culture was streaked on an agar culture medium having 1M sodium chloride and a culture was carried to pick up the grown strains. Thereafter, the picked-up grown cells were inoculated into a Erlenmeyer flask having a volume of 250 ml in which 100 ml of a liquid culture medium having 20% of glucose was loaded, and a shaking culture was carried out at 200 rpm for 120 hours, thereby obtaining the inventive low-oxygen-requiring T. madida mutant strain, named T. madida CJ-NT1.

The isolated T miadida CJ-NT1 has a rate of conversion to erythritol from glucose considerably higher than that of the parent KCTC 8712P strain under a low aeration condition. The inventive strain requires as low aeration rate as 60% of the parent strain in obtaining almost equivalent erythritol yield. In addition, the use of the inventive T. madida CJ-NT1 in preparing erythritol results in the considerably reduced occurrence of foaming at the time of culture. Therefore, a method for preparing erythritol from sugar with the use of the inventive T. madida CJ-NT1 makes it possible to increase a loading amount of a culture media in a fermentor to about 70% of the fermentor volume from about 50% of the fermentor volume, and thereby enables the erythritol productivity per unit volume of the fermentor to increase up to 40%.

The inventive T. madida CJ-NT1 strain has the following mycological properties:
1. State of Growth on Culture Media
    (1) Agar Slant (Yeast Malt agar culture medium)
    Color one: The colony turns from creamy to black with the lapse of time.
    (2) Microscopic Examination
    Shape of Vegetative Cells: Unicellular
    Propagation of Vegetative Cells: Budding
    Pseudomycelium: Formed (depending on culture conditions)
    Conidiospore: Formed
    Arthrospore: Formed
    Blastospore: Formed
2. Physiological Properties
    Growth Temperature: Up to about 40° C.
    Optimum Growth Temperature: 28 to 32° C.
    Growth pH: 2.5 to 8.0
    Optimum Growth pH: 4.0 to 7.0
    Decomposition of Urea: Found
    DBB (Diazonium B Blue) dyeing: Positive
    KNO3 Assimilation: Found
3. Fermentability of Sugars
    D-Glucose+
    Lactose−
    D-Galactose−
    Raffinose−
    L-Solbose−
    Maltose+
    Sucrose+
4. Assimilation of Sugars, Organic Acids and so on
    D-Glucose+
    D-Galactose−
    L-Solbose−
    Sucrose+
    Maltose+
    Cellobiose+
    Trehalose+
    Lactose−
    Melibiose−
    Raffinose+
    Melezitose−
    Inulin−
    D-Xylose+
    L-Arabinose+
    D-Arabinose−
    D-Ribose+
    L-Rhamnose+
    Glycerol+
    Erythritol+
    D-Mannitol+
    Methyl-α-D-Glucoside−
    Salicin−
    Lactate−
    Succinic Acid−
    Inositol−

The mycological properties of the inventive T. madida CJ-NT1 strain bears very close resemblance to those of the parent T. madida KCTC 8712P strain. In other words, the inventive mutant has the same mycological properties as those of the parent strain, except that the former demands considerably less oxygen at the time of culture.

The inventive T. madida CJ-NT1 strain are cultured on a liquid culture medium containing an assimilable carbon source, assimilable nitrogen source, inorganic salts and the like.

For the carbon source of the liquid culture media, fermentable saccharides such as glucose, fructose and sucrose may be used. As the nitrogen source, nitrogen compounds available by microorganisms are used such as yeast extract, corn steep liquor, peptone and urea. The inorganic salts used include salts such as ferrous sulfate, sodium chloride, dipotassium hydrogen phosphate, calcium hydroxide and zinc sulfate.

It is to be noted that in addition to these carbon sources, nitrogen sources and inorganic salts, various minerals in trace amount and antifoamer are required.

A temperature range suitable for culturing the inventive T. madida CJ-NT1 strain is 25° C. to 37° C. Preferably, culture is carried out at 30° C. to 32° C. The optimum pH for culture is about neutral pH.

The culture period in producing erythritol varies depending on the type of the media used and the concentration of sugars used as the carbon source, but is usually about 4 to 5 days. Referring to the mode of culture, it may be carried out either batchwise or continuously.

Erythritol accumulated in the culture solution may be separated therefrom in the conventional manner after the completion of culture. To this end, use may be made of the known means ordinary employed in the art such as filtration, centrifugation, ion exchange or adsorption chromatography, solvent extraction, distillation and crystallization which may suitably be combined, if required. By way of example, the cells are removed from the culture solution as by filtration or centrifugation, and the obtained solution is treated with activated charcoal to remove colored matters. Then, that solution is further deionized with an ion exchange resin, and is thereafter concentrated into a thick syrup, from which erythritol is finally separated by crystallization.

The embodiments of the present invention will now be explained further concretely with reference to the following examples.

EXAMPLE 1

Tolerance of wild-type *T Madida* and KCTC 8712P strain against the concentrations of sodium azide The wild-type *T madida* cells were applied over a slant culture medium comprising glucose, yeast extract and agar, and stationary culture was carried out at 30° C. for 72 hours. One platinum loop of the cultured cells was inoculated into a Erlenmeyer flask having a volume of 250 ml (loaded therein with 50 ml of a liquid culture medium containing Yeast Nitrogen Base(Difco), 1% (w/v) of glucose and 0 to 20 mg/l of sodium azide, any rotary shaking culture was carried out at 32° C. and 200 rpm for 120 hours. Optical absorbancy was measured to determine the inhibition effects of the concentrations of sodium azide on the growth of the cells. Separatively, the tolerance of the inventive *T. madida* KCTC 8712P cells against the concentrations of sodium azide was tested with the same manner as described above. The results are shown in Table I below.

TABLE I

| Sodium Azide Conc. (mg/l) | | 0 | 2 | 5 | 10 | 20 |
|---|---|---|---|---|---|---|
| *Relative Growth Ratio (%) | Wild Type | 100 | 21.4 | 15.2 | 0 | 0 |
| | KCTC 8712P | 100 | 55.9 | 46.1 | 6 | 0 |

$$*\text{Relative Growth Ratio} = \frac{\text{Optical absorbancy in each sodium azide conc.}}{\text{Optical absorbancy in mg/l sodium azide conc.}} \times 100$$

EXAMPLE 2

Effect of medium volumes on KCTC 8712P strain

The *T madida* KCTC 8712P cells were applied over a slant culture medium comprising glucose, yeast extract and agar, and stationary culture was carried out at 30° C. for 72 hours. One platinum loop of the cultured cells was inoculated into a Erlenmeyer flask having a volume of 250 ml (loaded therein with 30 ml, 50 ml, 70 ml or 100 ml of a liquid culture medium containing 40% of sugar, 1% of yeast extract and 0.1% of urea), and rotary shacking culture was carried out at 32° C. and 200 rpm for 120 hours. After the completion of culture, the amount of erythritol contained in each culture solution was measured by HPLC. The results are shown in Table II below.

TABLE II

| Medium Volume (ml) | Erythritol (g/l of culture solution) | Glucose (g/l of culture solution) |
|---|---|---|
| 30 | 188.3 | 0.0 |
| 50 | 185.0 | 0.2 |
| 70 | 157.2 | 19.2 |
| 100 | 118.5 | 56.3 |

EXAMPLE 3

Isolation of the inventive low-oxygen-requiring *T. madida* strain

The osmophilic *T. madida* KCTC 8712P cells were aerobically cultured on a liquid culture medium containing 20% (w/v) of glucose and 1% (w/v) of yeast extract for three (3) days. After centrifugation, the aqueous supernatant was discarded, and the sedimented microbes was diluted with the same sterile medium which was in turn treated whit 1 mg/ml of N-methyl-N'-nitro-N-nitrosoguanidine in a buffer solution. the thus treated cells were cultured on a liquid culture medium consisting of yeast Nitrogen Base (Difco), 1% (w/v) of glucose and 20 mg/l of sodium azide for 3 days. The culture was streaked on an agar culture medium containing IM sodium chloride, and stationary culture was carried out at 32° C. for 3 days to pick up the grown strains. Thereafter, forty grown colonies were selected and inoculated into each Erlenmeyer flask having a volume of 250 ml in which 100 ml of a liquid culture medium (pH 6.0) having 40% of glucose, 1% of yeast extract and 0.1% of urea was loaded, and shaking culture was carried out at 200 rpm for 120 hours to obtain a cultured product. After the completion of culture, the measurement of the concentration of erythritol in the culture solution revealed that four mutant cells had considerably higher erythritol productivity. Shaking cultures were repeated three times with the four mutant cells to pick up a mutant cell having the highest average erythritol productivity, thereby obtained the inventive osmophilic low-oxygen-requiring *T. madida* CJ-NT1 strain.

A 250 ml Erlenmeyer flask loaded with 100 ml of culture medium having 4 0% of glucose, 1% of yeast extract and 0.1% of urea was inoculated with the inventive *T. madida* CJ-NT1 cells, and shaking culture was carried out at 200 rpm for 100 hours under oxygen limited condition. After the completion of culture, the erythritol productivity was analyzed. Likewise, the parent *T madida* KCTC 8712P cells were shaking-cultured in the same manner as described above and, after the completion of culture, the erythritol productivity was analyzed. The results are shown in Table III below.

TABLE III

| Sugar amount in culture solution (g/l) | *T. madida* KCTC 8712P | *T. madida* CJ-NT1 |
|---|---|---|
| Erythritol | 121.5 | 186.4 |
| Glycerol | 39.2 | 18.4 |
| Glucose | 38.0 | 0.5 |

EXAMPLE 4

Effect of aeration rate on the erythritol productivity in 5 L fermentor

2 L of a culture medium (pH 6.0) containing 40% of glucose, 1% of yeast extract and 0.1% of urea was loaded into Fermentor No. 1 having a volume of 5 L, and was sterilized at 121° C. for 15 minutes. After cooling the culture medium, 150 ml of a seed culture solution of *T. madida* KCTC 8712P strain was added to the culture medium. Culture was then carried out at 32° C. and 600 rpm under an aeration of 0.3 vvm for 96 hours.

2 L of a culture medium (pH 6.0) containing 40% of glucose, 1% of yeast extract and 0.1% of urea was loaded into Fermenter No. 2 having a volume of 5 L, and was sterilized at 121° C. for 15 minutes. After cooling the culture medium, 150 ml of a seed culture solution of *T. madida* KCTC 8712P strain was added to the culture medium. Culture was then carried out at 32 C. and 600 rpm under an aeration of 0.5 vvm for 96 hours.

2 L of a culture medium (pH 6.0) containing 40% of glucose, 1% of yeast extract and 0.1% of urea was loaded into Fermenter No. 3 having a volume of 5 L, and was sterilized at 121° C. for 15 minutes. After cooling the culture medium, 150 ml of a seed culture solution of T madida CJ-NT1 strain was added to the culture medium. Culture was then carried out at 32C. and 600 rpm under an aeration of 0.3 vvm for 96 hours.

2 L of a culture medium (pH 6.0) containing 40% of glucose, 1% of yeast extract and 0.1% of urea was loaded into Fermenter No. 4 having a volume of 5 L, and was sterilized at 121° C. for 15 minutes After cooling the culture medium, 150 ml of a seed culture solution of T madida CJ-NT1 strain was added to the culture medium. Culture was then carried out at 32° C. and 600 rpm under and aeration of 0.5 vvm for 96 hours.

After the completion of culture in each fermenter, the analysis of the culture solution revealed the results shown in Table IV below.

TABLE IV

| Fermentor No. | 1 | 2 | 3 | 4 |
| --- | --- | --- | --- | --- |
| Strain | T. madida KCTC 8712P | | T. madida CJ-NT1 | |
| $O_2$ Conc. (vvm) | 0.3 | 0.5 | 0.3 | 0.5 |
| Erythritol (g/l of culture solution) | 138.5 | 179.3 | 182.3 | 185.5 |
| Glycerol (g/l of culture solution) | 35.6 | 23.0 | 20.3 | 18.8 |
| Glucose (g/l of culture solution) | 22.8 | 0.0 | 0.5 | 0.3 |

The above results demonstrate that the inventive T. madida CJ-NT1 strain can keep very high erythritol productivity under a low aeration rate.

EXAMPLE 5

Effect of medium volumes in 30 L fermentor on the erythritol productivity.

13 L of a culture medium (pH 6.0) containing 40% of glucose, 1% of yeast extract and 0.1% of urea was loaded into Fermentor No. 1 having a volume of 30 L, and was sterilized at 121° C. for 15 minutes. After cooling the culture medium, 1.0 L of a seed culture solution of T. madida CJ-NT1 strain was added to the culture medium. Culture was then carried out at 32° C. and 300 rpm under and aeration rate of 0.3 vvm for 96 hours.

13 L of a culture medium (pH 6.0) containing 40% of glucose, 1% of yeast extract and 0.1% of urea was loaded into Fermentor No. 2 having a volume of 30 L, and was sterilized at 121° C. for 15 minutes. After cooling the culture medium, 1.0 L of a seed culture solution of T. madida CJ-NT1 strain was added to the culture medium. Culture was then carried out at 32° C. and 300 rpm under an aeration rate of 0.5 wm for 96 hours.

17 L of a culture medium (pH 6.0) containing 40% of glucose, 1% of yeast extract and 0.1% of urea was loaded into Fermentor No. 3 having a volume of 30 L, and was sterilized at 121° C. for 15 minutes. After cooling the culture medium, 1.0 L of a seed culture solution of T madida CJ-NT1 strain was added to the culture medium. Culture was then carried out at 32° C. and 300 rpm under an aeration rate of 0.3 vvm for 96 hours.

17 L of a culture medium (pH 6.0) containing 40% of glucose, 1% of yeast extract and 0.1% of urea was loaded into Fermentor No. 4 having a volume of 30 L, and was sterilized at 121° C. for 15 minutes. After cooling the culture medium, 1.0 L of a seed culture solution of T. madida CJ-NTS strain was added to the culture medium. Culture was then carried out at 32 C. and 300 rpm under an aeration rate of 0.5 vvm for 96 hours.

After the completion of culture in each in each fermenter, the analysis of the culture solution revealed the results shown in Table V below.

Table V

What is claim is:

1. A method of producing erythritol by fermentation of sugar, which comprises culturing the cells of Trichosporonoides madida CJ-NT1 strain.

2. The method of claim 1, wherein the cells of Trichosporonoides maida CJ-NT1 are cultured in a liquid culture medium.

3. The method of claim 2, wherein the liquid culture medium comprises an assimilable carbon source, assimilable nitrogen source and inorganic salts.

4. The method of claim 3, wherein the carbon source comprises fermentable saccharides selected from the group consisting of glucose, fructose and sucrose.

5. The method of claim 3, wherein the nitrogen source is selected from the group consisting of yeast extract, corn steep liquor, peptone and urea.

6. The method of claim 3, wherein the inorganic salts are selected from the group consisting of ferrous sulfate, sodium chloride, dipotassium hydrogen phosphate, calcium hydroxide and zinc sulfate.

7. The method of claim 2, wherein the culture medium comprises an antifoamer.

8. The method of claim 2, wherein the culture medium comprises minerals.

9. The method of claim 1, wherein the cells of Trichosporonoides madida CJ-NT1 are cultured at a temperature of 25° C. to 37° C.

10. The method of claim 2, wherein the cells of Trichosporonoides madida CJ-NT1 are cultured for a period of 4 to 5 days.

11. The method of claim 1, wherein the cells of Trichosporonoides madida CJ-NT1 are cultured batchwise.

12. The method of claim 1, wherein the cells of Trichosporonoides madida CJ-NT1 are cultured continuously.

13. The method of claim 2, further comprising separating the erythritol produced from the culture medium.

14. The method of claim 13, wherein the separation employs a method selected from the group consisting of filtration, centrifugation, ion exchange chromatography, adsorption chromatography, solvent extraction, distillation, crystallization, and combination thereof.

* * * * *